(12) United States Patent
Chae et al.

(10) Patent No.: US 12,202,796 B2
(45) Date of Patent: Jan. 21, 2025

(54) METHOD FOR PREPARING 3(4),8(9)-BISFORMYLTRICYCLO[5.2.1.0$^{2,6}$]DECANE

(71) Applicant: SK CHEMICALS CO., LTD., Gyeonggi-do (KR)

(72) Inventors: Hee Il Chae, Seoul (KR); Jeong Ho Park, Gyeonggi-do (KR); Kyung Sil Yoon, Gyeonggi-do (KR); Ju-Sik Kang, Gyeonggi-do (KR); Yu Mi Chang, Gyeonggi-do (KR); Nam-Choul Yang, Seoul (KR); Jae Kyun Park, Seoul (KR); Song Lee, Seoul (KR)

(73) Assignee: SK Chemicals Co., Ltd., Gyeonggi-do (KR)

( * ) Notice: Subject to any disclaimer, the term of this patent is extended or adjusted under 35 U.S.C. 154(b) by 1078 days.

(21) Appl. No.: 16/973,130

(22) PCT Filed: May 31, 2019

(86) PCT No.: PCT/KR2019/006605
§ 371 (c)(1),
(2) Date: Dec. 8, 2020

(87) PCT Pub. No.: WO2019/240415
PCT Pub. Date: Dec. 19, 2019

(65) Prior Publication Data
US 2021/0253507 A1     Aug. 19, 2021

(30) Foreign Application Priority Data

Jun. 15, 2018  (KR) .................. 10-2018-0069247
May 30, 2019  (KR) .................. 10-2019-0063736

(51) Int. Cl.
| | | |
|---|---|---|
| *C07C 51/14* | (2006.01) |
| *B01J 23/46* | (2006.01) |
| *B01J 31/22* | (2006.01) |
| *C07C 51/44* | (2006.01) |
| *C07C 61/135* | (2006.01) |

(52) U.S. Cl.
CPC ............. *C07C 51/14* (2013.01); *B01J 23/464* (2013.01); *B01J 31/22* (2013.01); *C07C 51/44* (2013.01); *C07C 61/135* (2013.01); *C07C 2603/66* (2017.05)

(58) Field of Classification Search
None
See application file for complete search history.

(56) References Cited

U.S. PATENT DOCUMENTS

| | | |
|---|---|---|
| 3,499,933 A | 3/1970 | Pruett |
| 4,301,331 A | 11/1981 | Yurek |
| 5,041,675 A | 8/1991 | Lukas et al. |
| 5,138,101 A | 8/1992 | Devon |
| 6,365,782 B1 | 4/2002 | Nakamura et al. |
| 2005/0101805 A1 | 5/2005 | Lappe et al. |
| 2007/0100168 A1 | 5/2007 | Papp et al. |

FOREIGN PATENT DOCUMENTS

| | | |
|---|---|---|
| CN | 1636955 | 7/2005 |
| CN | 1890203 | 1/2007 |
| CN | 101679195 | 3/2010 |
| CN | 106542970 | 3/2017 |
| DE | 2819980 | 11/1979 |
| EP | 0023686 | 2/1981 |
| EP | 0059962 | 9/1982 |
| EP | 1065194 | 1/2001 |
| GB | 1170226 | 11/1969 |
| JP | 2001-011008 | 1/2001 |
| JP | 3712093 | 11/2005 |
| KR | 10-1992-0001988 | 3/1992 |
| KR | 10-2005-0044845 | 5/2005 |

OTHER PUBLICATIONS

Pruett "Industrial Organic Chemicals Through Utilization of Synthesis Gas," Annals of the New York Academy of Sciences, 1977, vol. 295, No. 1, pp. 239-248.
International Search Report and Written Opinion for International (PCT) Patent Application No. PCT/KR2019/006605, dated Sep. 11, 2019, 7 pages.
Translation of the International Search Report for International (PCT) Patent Application No. PCT/KR2019/006605, dated Sep. 11, 2019, 2 pages.

*Primary Examiner* — Ana Z Muresan
(74) *Attorney, Agent, or Firm* — Sheridan Ross P.C.

(57) ABSTRACT

A method of preparing 3(4),8(9)-bisformyltricyclo[5.2.1.0$^{2,6}$]decane is provided. According to the present invention, 3(4),8(9)-bisformyltricyclo[5.2.1.0$^{2,6}$]decane (TCDDA) may be prepared with a high conversion rate and purity without a separate catalyst recovery process.

11 Claims, No Drawings

METHOD FOR PREPARING 3(4),8(9)-BISFORMYLTRICYCLO[5.2.1.0$^{2,6}$]DECANE

CROSS-REFERENCE TO RELATED APPLICATION

This application is a national stage application under 35 U.S.C. 371 and claims the benefit of PCT Application No. PCT/KR2019/006605 having an international filing date of 31 May 2019, which designated the United States which PCT application claims the benefit of priority from, Korean Patent Application No. 10-2018-0069247 filed 15 Jun. 2018, and Korean Patent Application No. 10-2019-0063736, filed on May 30, 2019, the disclosures of which are hereby incorporated by reference herein in their entirety.

The present invention relates to a method of preparing 3(4),8(9)-bisformyltricyclo[5.2.1.0$^{2,6}$]decane.

BACKGROUND ART

3(4),8(9)-bisformyltricyclo[5.2.1.0$^{2,6}$]decane (TCD-dialdehyde, TCDDA) has particular properties due to a tricyclodecane (TCD) structure, and may be converted into compounds having important applications through further processing. For example, TCDDA may be converted into TCD-diamine {3(4),8(9)-bis(aminomethyl)tricyclo[5.2.1.0$^{2,6}$]decane} through reductive amination, and TCD-diamine may be used in the preparation of photostable polyurethane systems according to DE2819980 or in the preparation of thermally curable coating materials according to EP59962. Further, hydrogenation of TCDDA may be performed to prepare TCD-dimethanol {3(4),8(9)-dihydroxymethyltricyclo[5.2.1.02,6]decane} which is economically important as a constituent of acrylic ester adhesives that are curable in the absence of oxygen [see: EP23686].

TCDDA may be prepared by hydroformylation of dicyclopentadiene (DCP), which is a dimer of cyclopentadiene. In other words, TCDDA may be prepared by hydroformylation reaction of an olefin which introduces an aldehyde group by catalytic addition of carbon monoxide and hydrogen to a double bond of DCP.

A Co catalyst was initially used as a catalyst for the hydroformylation reaction, but it has been found that when the reaction is performed in the presence of a Rh catalyst, a higher conversion rate can be achieved under milder (lower temperature) conditions. Thus, the Rh catalyst has been mainly used. However, since Rh is an expensive precious metal, a process of recovering the RH catalyst is required when used in a large amount in order to ensure economic efficiency of the process. Therefore, there is a problem in that the entire process becomes complicated and efficiency becomes low.

The hydroformylation reaction of DCP is performed under high temperature and/or high pressure conditions, and in this case, there is also a problem in that a retro-Diels-Alder reaction of DCP occurs to generate cyclopentadiene, which reacts with DCP again to produce a cyclopentadiene oligomer. This reaction generates problems of consuming the reactant DCP and reducing purity of a final product.

Accordingly, there is a demand for a novel method of preparing TCDDA that is capable of minimizing loss due to the catalyst recovery process and side reactions such as the retro-Diels-Alder reaction.

PRIOR ART DOCUMENTS

Patent Documents

DE2819980
EP59962
EP23686

DISCLOSURE

Technical Problem

An object of the present invention is to provide a method capable of preparing TCDDA with a high yield and high purity by reducing side reactions while improving process efficiency without a need of a separate catalyst recovery process.

Technical Solution

To solve the above problems, the present invention provides a method of preparing 3(4),8(9)-bisformyltricyclo [5.2.1.0$^{2,6}$]decane, the method including the steps of:

performing a primary hydroformylation reaction while adding dicyclopentadiene dropwise to a reactor having a first temperature and a first pressure in the presence of a catalyst composition including a rhodium-containing catalyst compound and an organophosphorus compound; and performing a secondary hydroformylation reaction under a second temperature and a second pressure by increasing at least one of the pressure and the temperature of the reactor, after completing the primary hydroformylation reaction.

The primary and secondary hydroformylation reactions may be performed under a mixed gas atmosphere of hydrogen and carbon monoxide.

The second temperature may be 15° C. higher than the first temperature, and the second pressure may be 10 bar higher than the first pressure.

The first temperature may be 50° C. to 90° C., and the first pressure may be 20 bar to 130 bar.

The second temperature may be 80° C. to 180° C., and the second pressure may be 30 bar to 250 bar.

The dropwise addition of dicyclopentadiene may be performed such that the number of moles of dicyclopentadiene introduced per minute with respect to 1 mmol of the rhodium atoms in the catalyst composition may be 10 mmol to 10,000 mmol.

The rhodium-containing catalyst compound may be used in an amount of 1 ppm to 50 ppm in terms of rhodium, based on the total weight of the dicyclopentadiene.

The rhodium-containing catalyst compound and the organophosphorus compound may be included at a molar ratio of 1:2 to 1:500, in terms of rhodium and phosphorus atoms.

The rhodium-containing catalyst compound may be one or more selected from the group consisting of Rh(acac) (CO)$_2$, Rh$_2$O$_3$, Rh$_4$(CO)$_{12}$, Rh$_6$(CO)$_{16}$, Rh(NO$_3$)$_3$, Rh(CO$_2$(C1~C8)), Rh/Al, and Rh/C.

The organophosphorus compound may be one or more selected from the group consisting of triphenylphosphite, tris(2-t-butylphenyl)phosphite, tris(3-methyl-6-t-butylphenyl)phosphite, tris(3-methoxy-6-t-butylphenyl)phosphite, tris(2,4-di-t-butylphenyl)phosphite, and di(2-t-butylphenyl) phosphite.

A concentration of the catalyst composition may be 0.01 mM to 5.0 mM in terms of the rhodium atoms.

Effect of the Invention

According to a preparation method of the present invention, 3(4),8(9)-bisformyltricyclo[5.2.1.0$^{2,6}$]decane (TCDDA) may be prepared with a high conversion rate and purity in the presence of a small amount of a catalyst. Therefore, according to the present invention, a separate process of recovering a rhodium catalyst is not required, and high-purity TCDDA may be prepared without purification of a reaction mixture, thereby improving process efficiency and economic efficiency.

BEST MODE FOR CARRYING OUT THE INVENTION

Hereinafter, the present invention will be described in detail.

The present invention provides a method of preparing 3(4),8(9)-bisformyltricyclo[5.2.1.0$^{2,6}$]decane, the method including the steps of:

performing a primary hydroformylation reaction while adding dicyclopentadiene dropwise to a reactor having a first temperature and a first pressure in the presence of a catalyst composition including a rhodium-containing catalyst compound and an organophosphorus compound; and performing a secondary hydroformylation reaction under a second temperature and a second pressure by increasing at least one of the pressure and the temperature of the reactor, after completing the primary hydroformylation reaction.

The preparation method of the present invention may be performed by adding the raw material dicyclopentadiene (DCPD) dropwise to the catalyst composition and performing two stages of the hydroformylation reaction of dicyclopentadiene during the process of preparing TCDDA, thereby preparing TCDDA with a high conversion rate even using a much smaller amount of the rhodium catalyst than the amount of the rhodium catalyst used in the known method of preparing TCDDA. Thus, according to the present invention, a process of recovering the rhodium catalyst may be omitted, unlike the known method of preparing TCDDA, thereby increasing process efficiency and economic efficiency.

Further, according to the preparation method of the present invention, generation of by-products such as 8(9)-formylcyclo[5.2.1.0$^{2,6}$]-3-decene (TCD-monoaldehyde, TCDMA), a cyclopentadiene oligomer, etc. may be remarkably suppressed, thereby preparing high-purity TCDDA.

In the present invention, TCDDA may be prepared by a hydroformylation reaction of reacting DCPD with a mixed gas of hydrogen (2) and carbon monoxide (CO) in the presence of the catalyst composition including the rhodium (Rh) compound and the organophosphorus (P) compound. The hydroformylation reaction may be represented by the following Reaction Scheme 1.

[Reaction Scheme 1]

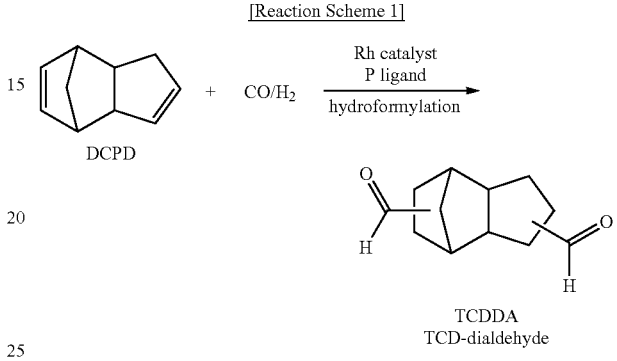

The DCPD may be prepared by a Diels-Alder reaction of cyclopentadiene (Cp), and it may be degraded into cyclopentadiene again at a high temperature by a retro-Diels-Alder reaction which is a reverse reaction of the Diels-Alder reaction. Therefore, when the reaction is performed at a high temperature, Cp produced by the retro-Diels-Alder reaction as in the following Reaction Scheme 2 may react with DCPD again by the Diels-Alder reaction to produce cyclopentadiene oligomers such as a cyclopentadiene trimer, etc., leading to hydroformylation of the oligomer. There is a problem in that this side reaction consumes DCPD to reduce a yield of TCDDA, and purity of TCDDA may be reduced due to generation of by-products.

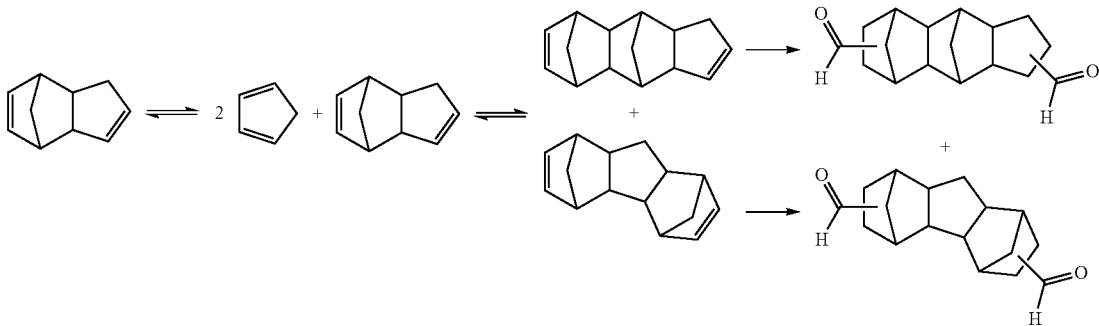

Accordingly, in the present invention, DCPD is added dropwise to the reactor to minimize production of Cp oligomers, and the primary hydroformylation reaction is first performed under relatively mild conditions, and then the secondary hydroformylation reaction is performed under higher temperature and/or pressure conditions to solve the above problems. In other words, in the present invention, the primary hydroformylation reaction is performed under relatively low temperature and pressure conditions, as compared with the conditions of the known method, while not adding DCPD at once but adding a small amount of DCPD dropwise to the reactor, and as a result, TCD-monoaldehyde (TCDMA) is first prepared as in the following Reaction Scheme 3, and Cp oligomerization which may occur when a high concentration of DCPD exists may be prevented. After completing the dropwise addition of DCPD, when the secondary hydroformylation may be performed by increasing the temperature and/or pressure of the reactor, hydroformylation of TCDMA may occur to prepare TCDDA. Therefore, according to the present invention, side reactions may be remarkably suppressed and the conversion rate into TCDDA may be greatly improved.

[Reaction Scheme 3]

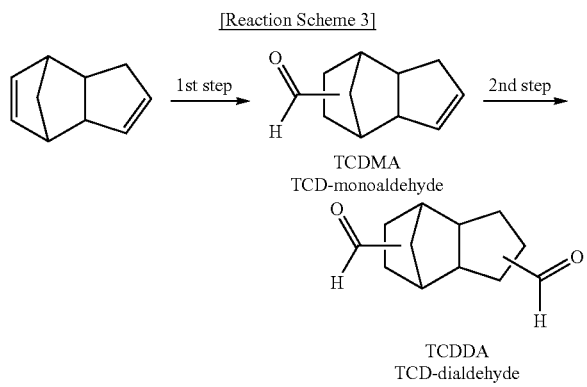

The hydroformylation reaction may be performed in the presence of the rhodium catalyst. The rhodium-containing catalyst compound applicable in the present invention is not particularly limited, as long as it forms a complex with the organophosphorus compound to exhibit a hydroformylation activity in the presence of hydrogen and carbon monoxide, and for example, one or more selected from the group consisting of $Rh(acac)(CO)_2$, $Rh_2O_3$, $Rh_4(CO)_{12}$, $Rh_6(CO)_{16}$, $Rh(NO_3)_3$, $Rh(CO_2(C1\sim C8))$, Rh/Al, and Rh/C may be used. Among them, $Rh(acac)(CO)_2$ may be preferably used.

In the known TCDDA preparation method, the rhodium compound has been commonly used in an amount of 70 ppm to 300 ppm in order to increase the conversion rate. However, when such a high concentration is used, a separate process of recovering the expensive rhodium catalyst is needed, and thus there is a problem in that the TCDDA preparation process may be deteriorated in terms of process efficiency and economic efficiency. However, in the present invention, hydroformylation is performed while not adding DCPD at once but adding a small amount of DCPD dropwise, and thus the excellent TCDDA conversion rate may be secured even using the remarkably reduced amount of the catalyst. Therefore, the separate catalyst recovery process is not required, thereby greatly improving process efficiency.

In the present invention, the rhodium-containing catalyst compound may be preferably used in an amount of 1 to 50 ppm, 10 to 35 ppm, or 10 to 20 ppm in terms of the rhodium atom, based on the total weight of the reactant dicyclopentadiene. If the amount of the rhodium-containing catalyst compound is less than 1 ppm based on the total weight of the dicyclopentadiene, the amount of the catalyst is too small, and thus the hydroformylation reaction may not properly occur to reduce the conversion rate. If the rhodium-containing catalyst compound is used in an excessive amount of more than 50 ppm, impurities may be produced due to side reactions, and the additional catalyst recovery process is required. Thus, the above-described effects may not be achieved. Accordingly, it is preferable that the amount of the catalyst satisfies the above range.

The rhodium-containing catalyst compound may exhibit the catalytic activity by forming a complex with the organophosphorus compound in an organic solvent. The organophosphorus compound applicable in the present invention may include phosphine, phosphite, etc., preferably, phosphite having a chemical formula of $P(-OR^1)(-OR^2)(-OR^3)$ (wherein $R^1$, $R^2$, and $R^3$ are each independently a substituted or unsubstituted alkyl group or aryl group). Specifically, the organophosphorus compound may include one or more selected from the group consisting of triphenylphosphite, tris(2-t-butylphenyl)phosphite, tris(3-methyl-6-t-butylphenyl)phosphite, tris(3-methoxy-6-t-butylphenyl)phosphite, tris(2,4-di-t-butylphenyl)phosphite, and di(2-t-butylphenyl)phosphite, but is not limited thereto.

The rhodium-containing catalyst compound and the organophosphorus compound may be preferably used at a molar ratio of 1:2 to 1:500, and more preferably, at a molar ratio of 1:3 to 1:200 or 1:5 to 1:100 in terms of rhodium and phosphorus atoms. If the molar ratio of the rhodium-containing catalyst compound and the organophosphorus compound is less than 1:2, a ligand required for the reaction is not sufficient, because two ligands must be theoretically reacted in the catalyst for the proper hydroformylation reaction. Thus, there is a problem in that reduction of the reactivity becomes severe. On the contrary, if the molar ratio is more than 1:500, the cost burden on the ligand is increased, and thus there is a problem in that the ligand recovery process must be additionally performed. Therefore, it is preferable that the molar ratio satisfies the above range.

The organic solvent applicable to the catalyst composition is not particularly limited, and a commonly known inert organic solvent may be used. Specifically, the organic solvent may include an aromatic hydrocarbon compound, an aliphatic hydrocarbon compound, and an alicyclic cyclic hydrocarbon compound.

The aromatic hydrocarbon compound may include benzene, methylbenzenes such as toluene, xylene, mesitylene, pseudocumene, etc., ethylbenzenes such as ethylbenzene, diethylbenzene, triethylbenzene, etc., propylbenzenes such as isopropylbenzene, 1,3-diisopropylbenzene, 1,4-diisopropylbenzene, etc., and other alkylbenzenes. The aliphatic hydrocarbon compound may include pentane, hexane, heptane, octane, isooctane, dodecane, and decane, but is not limited thereto as long as they are a liquid under normal temperature and pressure. The alicyclic hydrocarbon compound may include cyclohexane, cyclooctane, cyclododecane, decalin, methylcyclohexane, etc., which may be appropriately used.

A concentration of the catalyst composition is not particularly limited, for example, in the range of 0.01 mM to 5.0 mM, or 0.05 mM to 0.5 mM, in terms of the rhodium atoms. If the concentration of the catalyst composition is less than the above range, there is a problem in that the reactivity of the catalyst may be reduced due to the excessively low concentration. If the concentration of the catalyst composition is more than the above range, there is a problem in that the cost of the process may be increased due to the excess use of the catalyst. Therefore, the concentration is appropriately controlled within the above range.

After preparing the catalyst composition, the temperature and the pressure of the reactor may be adjusted to prepare the primary hydroformylation reaction.

In the present invention, the primary and secondary hydroformylation reactions may be performed under a mixed gas atmosphere of hydrogen and carbon monoxide. The pressure of the reactor may be adjusted by the pressure of the mixed gas of hydrogen and carbon monoxide. The first pressure may be preferably about 20 bar to 130 bar, and more preferably, about 30 bar to 120 bar, or 50 bar to 100 bar. If the first pressure is less than 20 bar, there is a problem in that the hydroformylation reaction may not properly occur. If the first pressure is more than 130 bar, there is a problem in that side reactions may occur due to a high partial pressure of hydrogen.

In this regard, for the proper hydroformylation reaction, a volume ratio of hydrogen and carbon monoxide is preferably 1:10 to 10:1, and more preferably 1:2 to 2:1.

The first temperature of the reactor is appropriately in the range of 50° C. to 90° C., and more appropriately in the range of 60° C. to 90° C., or 70° C. to 90° C. If the first temperature is too low (lower than 50° C.), the hydroformylation reaction may not proceed properly. If the first temperature is higher than 90° C., Cp oligomerization may occur due to retro-Diels-Alder reaction and Diels-Alder reaction, and thus it is preferable that the temperature is maintained within the above range.

After the pressure and the temperature of the reactor are maintained in the range suitable for the primary hydroformylation, a dicyclopentadiene stock solution (concentrate) or a dicyclopentadiene solution containing the organic solvent and dicyclopentadiene is introduced to the catalyst composition to perform the primary hydroformylation reaction.

The organic solvent included in the dicyclopentadiene solution may be an organic solvent applicable to the catalyst composition. The organic solvent used in the catalyst composition and the organic solvent used in the dicyclopentadiene solution are not necessarily the same as each other, but the same solvent may be preferably used to facilitate the reaction.

A concentration of the dicyclopentadiene solution is not particularly limited, but is, for example, in the range of 0.1 M or more, or 1.0 M to 7.6 M. If the concentration of the dicyclopentadiene solution is less than the above range, there is a problem in that the catalyst concentration of the catalyst composition is decreased with dropwise addition, and thus the hydroformylation reaction may not properly proceed. Therefore, the concentration is properly controlled within the above range.

In the present invention, to increase the reaction yield even in the presence of a small amount of the rhodium catalyst and to prevent side reactions by reducing the concentration of dicyclopentadiene in the reaction system, the dicyclopentadiene solution is added dropwise to the reactor. In this regard, a dropwise addition rate may be controlled according to the concentration of the dicyclopentadiene solution and the volume of the catalyst composition, and the number of moles of the dicyclopentadiene introduced per minute with respect to 1 mmol of the catalyst (in terms of the rhodium atoms) of the catalyst composition is preferably 10 mmol to 10,000 mmol, 100 mmol to 1000 mmol, or 100 mmol to 500 mmol.

If the dropwise addition rate is excessively higher than the above range, it is difficult to achieve the above-mentioned effects due to the generation of by-products, and if the dropwise addition rate is excessively lower than the above range, the overall reaction rate becomes slow to reduce process efficiency. Therefore, it is preferable that the dropwise addition rate satisfies the above range. The dropwise addition of the dicyclopentadiene solution and the primary hydroformylation are performed at the same time. However, to further improve the reaction rate, the reaction may be further performed under stirring for about 30 minutes or more, or for about 30 minutes to 2 hours, while maintaining the temperature and pressure conditions, after completing the dropwise addition.

TCDMA and TCDDA may be produced by the primary hydroformylation reaction, and to convert TCDMA into TCDDA by hydroformylation, the secondary hydroformylation reaction may be performed by increasing the temperature and/or the pressure.

When the secondary hydroformylation reaction is performed under the increased temperature condition, the second temperature may preferably be 15° C. higher, 25° C. higher, or 40° C. higher than the first temperature. Specifically, the second temperature may be in the range of 80° C. to 180° C., or 100° C. to 150° C., and preferably 110° C. to 135° C.

Further, when the secondary hydroformylation reaction is performed under the increased pressure condition, the second pressure may preferably be at least 10 bar higher, or 40 bar higher, than the first pressure. Specifically, the second pressure may be in the range of 30 bar to 250 bar, or 50 bar to 250 bar. Further, the secondary hydroformylation reaction may be performed by applying the temperature condition and the pressure condition at the same time, i.e., a temperature of 80° C. to 180° C. and a pressure of 30 bar to 250 bar.

The temperature and/or pressure conditions of the secondary hydroformylation step are sufficient to induce retro-Diels-Alder reaction of DCPD and subsequent oligomerization. However, in the present invention, the primary hydroformylation of DCPD may be performed under mild conditions, and thus almost all DCPDs are converted to TCDMA or TCDDA. Therefore, although the secondary hydroformylation is performed under the above conditions, there is no residual DCPD, and thus oligomer by-products of cyclopentadiene are not produced. Further, under the above conditions, TCDMA is converted to TCDDA by reacting with carbon monoxide and hydrogen gases, and thus TCDDA may be obtained with high yield and high purity.

Meanwhile, a purification step of purifying the product from the obtained reaction mixture after the secondary hydroformylation step may be further included. A method commonly known in the art may be employed in the purification step without limitation. For example, a vacuum distillation process may be employed. Before vacuum distillation, vacuum concentration may be preferably performed to remove the solvent from the reaction mixture. The vacuum distillation may be performed, for example, at a pressure of 0.1 Torr to 10 Torr, or 0.1 Torr to 1 Torr, and at a temperature of 90° C. to 150° C., or 100° C. to 120° C., but is not limited thereto.

According to the above-described method of preparing TCDDA of the present invention, TCDDA may be prepared using a remarkably reduced amount of the catalyst, as compared with the known method, and therefore no separate catalyst recovery process may be required, and production of the cyclopentadiene oligomers may be remarkably reduced to increase the conversion rate of TCDDA, thereby improving process efficiency and economic efficiency of the TCDDA preparation process.

Hereinafter, the actions and effects of the present invention will be described in more detail with reference to the specific examples. However, these examples are for illustrative purposes only, and the scope of the present invention is not intended to be limited by these examples.

EXAMPLE

Example 1

(Step 1)

In a 1 L high pressure reactor, 7.9 mg of $Rh(CO)_2(acac)$ (15 ppm in terms of Rh with respect to dicyclopentadiene) and 100 mg of tris(2,4-di-tert-butylphenyl)phosphite were dissolved in 100 g of toluene, and this mixture was heated to 85° C. while maintaining a pressure of a mixed gas of $CO:H_2=1:1$ at 100 bar. Thereafter, a DCPD solution prepared by mixing 10 g of toluene and 210 g of dicyclopentadiene (DCPD) was slowly added dropwise at a constant rate for 3 hours such that the amount of DCPD added dropwise per minute was 320 mmol with respect to 1 mmol of Rh. During the dropwise addition of the DCPD solution, the temperature and the pressure inside the high pressure reactor were maintained at 85° C. and 100 bar, respectively. After completing the dropwise addition of the DCPD solution, reaction was further allowed for 1.5 hours under the same temperature and pressure conditions.

(Step 2)

The reaction mixture of step 1 was heated to 130° C. without additional purification, and reaction was further allowed for 3 hours while maintaining the pressure of the mixed gas of $CO/H_2$ at 100 bar. Thereafter, the reaction mixture sample was collected and analyzed by gas chromatography.

(Step 3)

The reaction mixture of step 2 was concentrated under vacuum to remove toluene. The mixture from which toluene had been removed was vacuum-distilled under conditions of 0.5 Torr and 110° C. to obtain 281.1 g of a desired compound, TCDDA (TCD-dialdehyde) (yield: 92.0%).

Example 2

(Step 1)

In a 1 L high pressure reactor, 7.9 mg of $Rh(CO)_2(acac)$ (15 ppm in terms of Rh with respect to dicyclopentadiene) and 100 mg of tris(2,4-di-tert-butylphenyl)phosphite were dissolved in 100 g of toluene, and this mixture was heated to 85° C. while maintaining a pressure of a mixed gas of $CO:H_2=1:1$ at 100 bar. Thereafter, a DCPD solution prepared by mixing 10 g of toluene and 210 g of dicyclopentadiene (DCPD) was slowly added dropwise at a constant rate for 3 hours such that the amount of DCPD added dropwise per minute was 320 mmol with respect to 1 mmol of Rh. During the dropwise addition of the DCPD solution, the temperature and the pressure inside the high pressure reactor were maintained at 85° C. and 100 bar, respectively. After completing the dropwise addition of the DCPD solution, reaction was further allowed for 1.5 hours under the same temperature and pressure conditions.

(Step 2)

The reaction mixture of step 1 was heated to 110° C. without additional purification, and reaction was further allowed for 15 hours while maintaining the pressure of the mixed gas of $CO/H_2$ at 100 bar. Thereafter, the reaction mixture sample was collected and analyzed by gas chromatography.

(Step 3)

The reaction mixture of step 2 was concentrated under vacuum to remove toluene. The mixture from which toluene had been removed was vacuum-distilled under conditions of 0.5 Torr and 110° C. to obtain 281.9 g of a desired compound, TCDDA (TCD-dialdehyde) (yield: 92.3%).

Example 3

(Step 1)

In a 1 L high pressure reactor, 7.9 mg of $Rh(CO)_2(acac)$ (15 ppm in terms of Rh with respect to dicyclopentadiene) and 1.0 g of tris(2,4-di-tert-butylphenyl)phosphite were dissolved in 100 g of toluene, and this mixture was heated to 85° C. while maintaining a pressure of a mixed gas of $CO:H_2=1:1$ at 100 bar. Thereafter, a DCPD solution prepared by mixing 10 g of toluene and 210 g of dicyclopentadiene (DCPD) was slowly added dropwise at a constant rate for 3 hours such that the amount of DCPD added dropwise per minute was 320 mmol with respect to 1 mmol of Rh. During the dropwise addition of the DCPD solution, the temperature and the pressure inside the high pressure reactor were maintained at 85° C. and 100 bar, respectively. After completing the dropwise addition of the DCPD solution, reaction was further allowed for 1.5 hours under the same temperature and pressure conditions.

(Step 2)

The reaction mixture of step 1 was heated to 130° C. without additional purification, and reaction was further allowed for 3 hours while maintaining the pressure of the mixed gas of $CO/H_2$ at 100 bar. Thereafter, the reaction mixture sample was collected and analyzed by gas chromatography.

(Step 3)

The reaction mixture of step 2 was concentrated under vacuum to remove toluene. The mixture from which toluene had been removed was vacuum-distilled under conditions of 0.5 Torr and 110° C. to obtain 287.6 g of a desired compound, TCDDA (TCD-dialdehyde) (yield: 91.2%).

Example 4

(Step 1)

In a 1 L high pressure reactor, 7.9 mg of $Rh(CO)_2(acac)$ (15 ppm in terms of Rh with respect to dicyclopentadiene) and 0.5 g of tris(2,4-di-tert-butylphenyl)phosphite were dissolved in 100 g of toluene, and this mixture was heated to 85° C. while maintaining a pressure of a mixed gas of $CO:H_2=1:1$ at 100 bar. Thereafter, a DCPD solution prepared by mixing 10 g of toluene and 210 g of dicyclopentadiene (DCPD) was slowly added dropwise at a constant rate for 3 hours such that the amount of DCPD added dropwise per minute was 320 mmol with respect to 1 mmol of Rh. During the dropwise addition of the DCPD solution, the temperature and the pressure inside the high pressure reactor were maintained at 85° C. and 100 bar, respectively. After completing the dropwise addition of the DCPD solution, reaction was further allowed for 1.5 hours under the same temperature and pressure conditions.

(Step 2)

The reaction mixture of step 1 was heated to 130° C. without additional purification, and reaction was further allowed for 4 hours while maintaining the pressure of the mixed gas of $CO/H_2$ at 100 bar. Thereafter, the reaction mixture sample was collected and analyzed by gas chromatography.

(Step 3)

The reaction mixture of step 2 was concentrated under vacuum to remove toluene. The mixture from which toluene had been removed was vacuum-distilled under conditions of 0.5 Torr and 110° C. to obtain 263.6 g of a desired compound, TCDDA (TCD-dialdehyde) (yield: 86.3%).

Example 5

(Step 1)
In a 1 L high pressure reactor, 7.9 mg of $Rh(CO)_2(acac)$ (15 ppm in terms of Rh with respect to dicyclopentadiene) and 0.3 g of tris(2,4-di-tert-butylphenyl)phosphite were dissolved in 100 g of toluene, and this mixture was heated to 85° C. while maintaining a pressure of a mixed gas of $CO:H_2=1:1$ at 100 bar. Thereafter, a DCPD solution prepared by mixing 10 g of toluene and 210 g of dicyclopentadiene (DCPD) was slowly added dropwise at a constant rate for 3 hours such that the amount of DCPD added dropwise per minute was 320 mmol with respect to 1 mmol of Rh. During the dropwise addition of the DCPD solution, the temperature and the pressure inside the high pressure reactor were maintained at 85° C. and 100 bar, respectively. After completing the dropwise addition of the DCPD solution, reaction was further allowed for 1.5 hours under the same temperature and pressure conditions.

(Step 2)
The reaction mixture of step 1 was heated to 130° C. without additional purification, and reaction was further allowed for 3 hours while maintaining the pressure of the mixed gas of $CO/H_2$ at 100 bar. Thereafter, the reaction mixture sample was collected and analyzed by gas chromatography.

(Step 3)
The reaction mixture of step 2 was concentrated under vacuum to remove toluene. The mixture from which toluene had been removed was vacuum-distilled under conditions of 0.5 Torr and 110° C. to obtain 264.3 g of a desired compound, TCDDA (TCD-dialdehyde) (yield: 86.5%).

Example 6

(Step 1)
In a 1 L high pressure reactor, 7.9 mg of $Rh(CO)_2(acac)$ (15 ppm in terms of Rh with respect to dicyclopentadiene) and 2.0 g of tris(2,4-di-tert-butylphenyl)phosphite were dissolved in 100 g of toluene, and this mixture was heated to 75° C. while maintaining a pressure of a mixed gas of $CO:H_2=1:1$ at 100 bar. Thereafter, a DCPD solution prepared by mixing 10 g of toluene and 210 g of dicyclopentadiene (DCPD) was slowly added dropwise at a constant rate for 3 hours such that the amount of DCPD added dropwise per minute was 320 mmol with respect to 1 mmol of Rh. During the dropwise addition of the DCPD solution, the temperature and the pressure inside the high pressure reactor were maintained at 75° C. and 100 bar, respectively. After completing the dropwise addition of the DCPD solution, reaction was further allowed for 1.5 hours under the same temperature and pressure conditions.

(Step 2)
The reaction mixture of step 1 was heated to 130° C. without additional purification, and reaction was further allowed for 3 hours while maintaining the pressure of the mixed gas of $CO/H_2$ at 100 bar. Thereafter, the reaction mixture sample was collected and analyzed by gas chromatography.

(Step 3)
The reaction mixture of step 2 was concentrated under vacuum to remove toluene. The mixture from which toluene had been removed was vacuum-distilled under conditions of 0.5 Torr and 110° C. to obtain 281.4 g of a desired compound, TCDDA (TCD-dialdehyde) (yield: 92.1%).

Example 7

(Step 1)
In a 1 L high pressure reactor, 7.9 mg of $Rh(CO)_2(acac)$ (15 ppm in terms of Rh with respect to dicyclopentadiene) and 0.5 g of tris(2,4-di-tert-butylphenyl)phosphite were dissolved in 100 g of toluene, and this mixture was heated to 75° C. while maintaining a pressure of a mixed gas of $CO:H_2=1:1$ at 100 bar. Thereafter, a DCPD solution prepared by mixing 10 g of toluene and 210 g of dicyclopentadiene (DCPD) was slowly added dropwise at a constant rate for 3 hours such that the amount of DCPD added dropwise per minute was 320 mmol with respect to 1 mmol of Rh. During the dropwise addition of the DCPD solution, the temperature and the pressure inside the high pressure reactor were maintained at 75° C. and 100 bar, respectively. After completing the dropwise addition of the DCPD solution, reaction was further allowed for 1.5 hours under the same temperature and pressure conditions.

(Step 2)
The reaction mixture of step 1 was heated to 130° C. without additional purification, and reaction was further allowed for 3 hours while maintaining the pressure of the mixed gas of $CO/H_2$ at 100 bar. Thereafter, the reaction mixture sample was collected and analyzed by gas chromatography.

(Step 3)
The reaction mixture of step 2 was concentrated under vacuum to remove toluene. The mixture from which toluene had been removed was vacuum-distilled under conditions of 0.5 Torr and 110° C. to obtain 264.0 g of a desired compound, TCDDA (TCD-dialdehyde) (yield: 86.4%).

Example 8

(Step 1)
In a 1 L high pressure reactor, 7.9 mg of $Rh(CO)_2(acac)$ (15 ppm in terms of Rh with respect to dicyclopentadiene) and 0.3 g of tris(2,4-di-tert-butylphenyl)phosphite were dissolved in 100 g of toluene, and this mixture was heated to 75° C. while maintaining a pressure of a mixed gas of $CO:H_2=1:1$ at 100 bar. Thereafter, a DCPD solution prepared by mixing 10 g of toluene and 210 g of dicyclopentadiene (DCPD) was slowly added dropwise at a constant rate for 3 hours such that the amount of DCPD added dropwise per minute was 320 mmol with respect to 1 mmol of Rh. During the dropwise addition of the DCPD solution, the temperature and the pressure inside the high pressure reactor were maintained at 75° C. and 100 bar, respectively. After completing the dropwise addition of the DCPD solution, reaction was further allowed for 1.5 hours under the same temperature and pressure conditions.

(Step 2)
The reaction mixture of step 1 was heated to 130° C. without additional purification, and reaction was further allowed for 3 hours while maintaining the pressure of the mixed gas of $CO/H_2$ at 100 bar. Thereafter, the reaction mixture sample was collected and analyzed by gas chromatography.

(Step 3)
The reaction mixture of step 2 was concentrated under vacuum to remove toluene. The mixture from which toluene had been removed was vacuum-distilled under conditions of 0.5 Torr and 110° C. to obtain 266.2 g of a desired compound, TCDDA (TCD-dialdehyde) (yield: 87.2%).

Example 9

(Step 1)

In a 1 L high pressure reactor, 7.9 mg of $Rh(CO)_2(acac)$ (15 ppm in terms of Rh with respect to dicyclopentadiene) and 2.0 g of tris(2,4-di-tert-butylphenyl)phosphite were dissolved in 100 g of toluene, and this mixture was heated to 85° C. while maintaining a pressure of a mixed gas of $CO:H_2=1:1$ at 70 bar. Thereafter, a DCPD solution prepared by mixing 10 g of toluene and 210 g of dicyclopentadiene (DCPD) was slowly added dropwise at a constant rate for 3 hours such that the amount of DCPD added dropwise per minute was 320 mmol with respect to 1 mmol of Rh. During the dropwise addition of the DCPD solution, the temperature and the pressure inside the high pressure reactor were maintained at 85° C. and 70 bar, respectively. After completing the dropwise addition of the DCPD solution, reaction was further allowed for 1.5 hours under the same temperature and pressure conditions.

(Step 2)

The reaction mixture of step 1 was heated to 130° C. without additional purification, and reaction was further allowed for 3 hours while maintaining the pressure of the mixed gas of $CO/H_2$ at 70 bar. Thereafter, the reaction mixture sample was collected and analyzed by gas chromatography.

(Step 3)

The reaction mixture of step 2 was concentrated under vacuum to remove toluene. The mixture from which toluene had been removed was vacuum-distilled under conditions of 0.5 Torr and 110° C. to obtain 284.4 g of a desired compound, TCDDA (TCD-dialdehyde) (yield: 93.1%).

Example 10

(Step 1)

In a 1 L high pressure reactor, 7.9 mg of $Rh(CO)_2(acac)$ (15 ppm in terms of Rh with respect to dicyclopentadiene) and 2.0 g of tris(2,4-di-tert-butylphenyl)phosphite were dissolved in 100 g of toluene, and this mixture was heated to 85° C. while maintaining a pressure of a mixed gas of $CO:H_2=1:1$ at 50 bar. Thereafter, a DCPD solution prepared by mixing 10 g of toluene and 210 g of dicyclopentadiene (DCPD) was slowly added dropwise at a constant rate for 3 hours such that the amount of DCPD added dropwise per minute was 320 mmol with respect to 1 mmol of Rh. During the dropwise addition of the DCPD solution, the temperature and the pressure inside the high pressure reactor were maintained at 85° C. and 50 bar, respectively. After completing the dropwise addition of the DCPD solution, reaction was further allowed for 1.5 hours under the same temperature and pressure conditions.

(Step 2)

The reaction mixture of step 1 was heated to 130° C. without additional purification, and reaction was further allowed for 3 hours while maintaining the pressure of the mixed gas of $CO/H_2$ at 50 bar. Thereafter, the reaction mixture sample was collected and analyzed by gas chromatography.

(Step 3)

The reaction mixture of step 2 was concentrated under vacuum to remove toluene. The mixture from which toluene had been removed was vacuum-distilled under conditions of 0.5 Torr and 110° C. to obtain 284.7 g of a desired compound, TCDDA (TCD-dialdehyde) (yield: 93.2%).

Example 11

(Step 1)

In a 1 L high pressure reactor, 7.9 mg of $Rh(CO)_2(acac)$ (15 ppm in terms of Rh with respect to dicyclopentadiene) and 2.0 g of tris(2,4-di-tert-butylphenyl)phosphite were dissolved in 100 g of toluene, and this mixture was heated to 85° C. while maintaining a pressure of a mixed gas of $CO:H_2=1:1$ at 30 bar. Thereafter, a DCPD solution prepared by mixing 10 g of toluene and 210 g of dicyclopentadiene (DCPD) was slowly added dropwise at a constant rate for 3 hours such that the amount of DCPD added dropwise per minute was 320 mmol with respect to 1 mmol of Rh. During the dropwise addition of the DCPD solution, the temperature and the pressure inside the high pressure reactor were maintained at 85° C. and 30 bar, respectively. After completing the dropwise addition of the DCPD solution, reaction was further allowed for 1.5 hours under the same temperature and pressure conditions.

(Step 2)

The reaction mixture of step 1 was heated to 130° C. without additional purification, and reaction was further allowed for 3 hours while maintaining the pressure of the mixed gas of $CO/H_2$ at 30 bar. Thereafter, the reaction mixture sample was collected and analyzed by gas chromatography.

(Step 3)

The reaction mixture of step 2 was concentrated under vacuum to remove toluene. The mixture from which toluene had been removed was vacuum-distilled under conditions of 0.5 Torr and 110° C. to obtain 278.3 g of a desired compound, TCDDA (TCD-dialdehyde) (yield: 91.1%).

Example 12

(Step 1)

In a 1 L high pressure reactor, 7.9 mg of $Rh(CO)_2(acac)$ (15 ppm in terms of Rh with respect to dicyclopentadiene) and 2.0 g of tris(2,4-di-tert-butylphenyl)phosphite were dissolved in 100 g of toluene, and this mixture was heated to 85° C. while maintaining a pressure of a mixed gas of $CO:H_2=1:1$ at 20 bar. Thereafter, a DCPD solution prepared by mixing 10 g of toluene and 210 g of dicyclopentadiene (DCPD) was slowly added dropwise at a constant rate for 3 hours such that the amount of DCPD added dropwise per minute was 320 mmol with respect to 1 mmol of Rh. During the dropwise addition of the DCPD solution, the temperature and the pressure inside the high pressure reactor were maintained at 85° C. and 20 bar, respectively. After completing the dropwise addition of the DCPD solution, reaction was further allowed for 1.5 hours under the same temperature and pressure conditions.

(Step 2)

The reaction mixture of step 1 was heated to 130° C. without additional purification, and reaction was further allowed for 3 hours while maintaining the pressure of the mixed gas of $CO/H_2$ at 20 bar. Thereafter, the reaction mixture sample was collected and analyzed by gas chromatography.

(Step 3)

The reaction mixture of step 2 was concentrated under vacuum to remove toluene. The mixture from which toluene had been removed was vacuum-distilled under conditions of 0.5 Torr and 110° C. to obtain 261.2 g of a desired compound, TCDDA (TCD-dialdehyde) (yield: 85.5%).

Example 13

(Step 1)

In a 1 L high pressure reactor, 3.9 mg of $Rh(CO)_2(acac)$ (7.5 ppm in terms of Rh with respect to dicyclopentadiene) and 2.0 g of tris(2,4-di-tert-butylphenyl)phosphite were dissolved in 100 g of toluene, and this mixture was heated to 85° C. while maintaining a pressure of a mixed gas of $CO:H_2=1:1$ at 100 bar. Thereafter, a DCPD solution prepared by mixing 10 g of toluene and 210 g of dicyclopentadiene (DCPD) was slowly added dropwise at a constant rate for 3 hours such that the amount of DCPD added dropwise per minute was 320 mmol with respect to 1 mmol of Rh. During the dropwise addition of the DCPD solution, the temperature and the pressure inside the high pressure reactor were maintained at 85° C. and 100 bar, respectively. After completing the dropwise addition of the DCPD solution, reaction was further allowed for 1.5 hours under the same temperature and pressure conditions.

(Step 2)

The reaction mixture of step 1 was heated to 130° C. without additional purification, and reaction was further allowed for 3 hours while maintaining the pressure of the mixed gas of $CO/H_2$ at 100 bar. Thereafter, the reaction mixture sample was collected and analyzed by gas chromatography.

(Step 3)

The reaction mixture of step 2 was concentrated under vacuum to remove toluene. The mixture from which toluene had been removed was vacuum-distilled under conditions of 0.5 Torr and 110° C. to obtain 280.8 g of a desired compound, TCDDA (TCD-dialdehyde) (yield: 91.1%).

Example 14

(Step 1)

In a 1 L high pressure reactor, 7.9 mg of $Rh(CO)_2(acac)$ (15 ppm in terms of Rh with respect to dicyclopentadiene) and 2.0 g of tris(2,4-di-tert-butylphenyl)phosphite were dissolved in 100 g of toluene, and this mixture was heated to 80° C. while maintaining a pressure of a mixed gas of $CO:H_2=1:1$ at 100 bar. Thereafter, a DCPD solution prepared by mixing 10 g of toluene and 210 g of dicyclopentadiene (DCPD) was slowly added dropwise at a constant rate for 3 hours such that the amount of DCPD added dropwise per minute was 320 mmol with respect to 1 mmol of Rh. During the dropwise addition of the DCPD solution, the temperature and the pressure inside the high pressure reactor were maintained at 80° C. and 100 bar, respectively. After completing the dropwise addition of the DCPD solution, reaction was further allowed for 1.5 hours under the same temperature and pressure conditions.

(Step 2)

The reaction mixture of step 1 was further reacted for 20 hours without additional purification while increasing the pressure of the mixed gas of $CO/H_2$ to 180 bar and maintaining the temperature at 80° C. Thereafter, the reaction mixture sample was collected and analyzed by gas chromatography.

(Step 3)

The reaction mixture of step 2 was concentrated under vacuum to remove toluene. The mixture from which toluene had been removed was vacuum-distilled under conditions of 0.5 Torr and 110° C. to obtain 269.8 g of a desired compound, TCDDA (TCD-dialdehyde) (yield: 88.3%).

Example 15

(Step 1)

In a 1 L high pressure reactor, 7.9 mg of $Rh(CO)_2(acac)$ (15 ppm in terms of Rh with respect to dicyclopentadiene) and 2.0 g of tris(2,4-di-tert-butylphenyl)phosphite were dissolved in 100 g of toluene, and this mixture was heated to 90° C. while maintaining a pressure of a mixed gas of $CO:H_2=1:1$ at 80 bar. Thereafter, a DCPD solution prepared by mixing 10 g of toluene and 210 g of dicyclopentadiene (DCPD) was slowly added dropwise at a constant rate for 3 hours such that the amount of DCPD added dropwise per minute was 320 mmol with respect to 1 mmol of Rh. During the dropwise addition of the DCPD solution, the temperature and the pressure inside the high pressure reactor were maintained at 90° C. and 80 bar, respectively. After completing the dropwise addition of the DCPD solution, reaction was further allowed for 1.5 hours under the same temperature and pressure conditions.

(Step 2)

The reaction mixture of step 1 was further reacted for 22 hours without additional purification while increasing the pressure of the mixed gas of $CO/H_2$ to 130 bar and maintaining the temperature at 90° C. Thereafter, the reaction mixture sample was collected and analyzed by gas chromatography.

(Step 3)

The reaction mixture of step 2 was concentrated under vacuum to remove toluene. The mixture from which toluene had been removed was vacuum-distilled under conditions of 0.5 Torr and 110° C. to obtain 271.6 g of a desired compound, TCDDA (TCD-dialdehyde) (yield: 88.9%).

Comparative Example 1

In a 1 L high pressure reactor, 150 mg of $Rh(CO)_2(acac)$ and 1.88 g of tris(2,4-di-tert-butylphenyl)phosphite were dissolved in 150 g of cyclohexane, and this mixture was heated to 130° C. while maintaining a pressure of a mixed gas of $CO:H_2=1:1$ at 100 bar. Thereafter, a mixture of 10 g of cyclohexane and 250 g of dicyclopentadiene (DCPD) was slowly added dropwise to the high pressure reactor at a rate of 2.2 ml/min (i.e., 29 mmol of DCPD per minute was added with respect to 1 mmol of Rh) for 2 hours. During the dropwise addition of the DCPD solution, the temperature and the pressure inside the high pressure reactor were maintained at 130° C. and 100 bar, respectively. After completing the dropwise addition of the DCPD solution, reaction was further allowed for 3 hours. Thereafter, the reaction mixture sample was collected and analyzed by gas chromatography.

After collecting the sample, the remainder of the reaction mixture was concentrated under vacuum to remove toluene. The mixture from which toluene had been removed was vacuum-distilled under conditions of 0.5 Torr and 110° C. to obtain 168.9 g of a desired compound, TCDDA (TCD-dialdehyde) (yield: 55.3%).

Comparative Example 2

In a 1 L high pressure reactor, 7.9 mg of $Rh(CO)_2(acac)$ and 2.0 g of tris(2,4-di-tert-butylphenyl)phosphite were dissolved in 100 g of toluene, and this mixture was heated to 130° C. while maintaining a pressure of a mixed gas of CO:H$_2$=1:1 at 100 bar. Thereafter, a DCPD solution prepared by mixing 10 g of toluene and 210 g of dicyclopentadiene (DCPD) was slowly added dropwise at a constant rate for 2 hours such that the amount of DCPD added dropwise per minute was 320 mmol with respect to 1 mmol of Rh. During the dropwise addition of the DCPD solution, the temperature and the pressure inside the high pressure reactor were maintained at 130° C. and 100 bar, respectively. After completing the dropwise addition of the DCPD solution, reaction was further allowed for 3 hours under the same temperature and pressure conditions. Thereafter, the reaction mixture sample was collected and analyzed by gas chromatography.

After collecting the sample, the remainder of the reaction mixture was concentrated under vacuum to remove toluene. The mixture from which toluene had been removed was vacuum-distilled under conditions of 0.5 Torr and 110° C. to obtain 151.2 g of a desired compound, TCDDA (TCD-dialdehyde) (yield: 49.5%).

Comparative Example 3

(Step 1)

In a 1 L high pressure reactor, 7.9 mg of Rh(CO)$_2$(acac) (15 ppm in terms of Rh with respect to dicyclopentadiene) and 2.0 g of tris(2,4-di-tert-butylphenyl)phosphite were dissolved in 100 g of toluene, and then 210 g of dicyclopentadiene (DCPD) was not added dropwise but added at once. The reaction mixture was reacted for 3 hours while heating to 85° C. and maintaining a pressure of a mixed gas of CO:H$_2$=1:1 at 100 bar.

(Step 2)

Without additional purification, the reaction mixture of step 1 was further reacted for 3 hours while heating to 130° C. and maintaining the pressure of the mixed gas of CO/H$_2$ at 100 bar. Thereafter, the reaction mixture sample was collected and analyzed by gas chromatography.

(Step 3)

The reaction mixture of step 2 was concentrated under vacuum to remove toluene. The mixture from which toluene had been removed was vacuum-distilled under conditions of 0.5 Torr and 110° C. to obtain 220.6 g of a desired compound, TCDDA (TCD-dialdehyde) (yield: 72.2%).

Results of analyzing the reaction mixtures of Examples and Comparative Examples by gas chromatography are shown in Table 1 below.

TABLE 1

| | Reaction conditions | | | | | | GC area of reaction mixture (%) | | | |
| --- | --- | --- | --- | --- | --- | --- | --- | --- | --- | --- |
| | Temperature of first step (° C.) | Temperature of second step (° C.) | Pressure of first step (bar) | Pressure of second step (bar) | Ligand (eq) | Rh (ppm) | TCDMA | TCDDA | TCDAA | CP oligomers + Hydrofomylated CP oligomers |
| Comparative Example 1 | 130 | | 100 | | 5 | 400 | 1.1 | 63.1 | 0.1 | 35.7 |
| Comparative Example 2 | 130 | | 100 | | 100 | 15 | 0.8 | 58.3 | 1.4 | 41.2 |
| Comparative Example 3 | 85 | 130 | 100 | | 100 | 15 | 0.9 | 79.1 | 2.6 | 14.5 |
| Example 1 | 85 | 130 | 100 | | 100 | 15 | 0.3 | 94.9 | 2.7 | 0.1 |
| Example 2 | 85 | 110 | 100 | | 100 | 15 | 0.4 | 95.1 | 0.8 | 0.2 |
| Example 3 | 85 | 130 | 100 | | 50 | 15 | 0.9 | 94.0 | 1.9 | 0.2 |
| Example 4 | 85 | 130 | 100 | | 25 | 15 | 1.2 | 89.8 | 3.9 | 2.3 |
| Example 5 | 85 | 130 | 100 | | 15 | 15 | 1.0 | 89.0 | 3.5 | 4.0 |
| Example 6 | 75 | 130 | 100 | | 100 | 15 | 0.3 | 94.6 | 2.9 | 0.1 |
| Example 7 | 75 | 130 | 100 | | 25 | 15 | 1.2 | 89.4 | 4.4 | 2.7 |
| Example 8 | 75 | 130 | 100 | | 15 | 15 | 1.0 | 89.9 | 3.3 | 3.8 |
| Example 9 | 85 | 130 | 70 | | 100 | 15 | 0.5 | 93.6 | 2.5 | 0.1 |
| Example 10 | 85 | 130 | 50 | | 100 | 15 | 0.4 | 94.7 | 1.8 | 0.2 |
| Example 11 | 85 | 130 | 30 | | 100 | 15 | 0.4 | 92.3 | 1.7 | 2.5 |
| Example 12 | 85 | 130 | 20 | | 100 | 15 | 0.5 | 85.2 | 1.6 | 10.2 |
| Example 13 | 85 | 130 | 100 | | 200 | 7.5 | 0.5 | 94.3 | 1.5 | 0.3 |
| Example 14 | | 80 | 100 | 180 | 100 | 15 | 3.5 | 91.5 | 0.5 | 0.3 |
| Example 15 | | 90 | 80 | 130 | 100 | 15 | 2.3 | 92.3 | 1.0 | 0.2 |

* Rh (ppm): Content of Rh atoms in catalyst, with respect to dicyclopentadiene
* Ligand (eq): Molar equivalent with respect to Rh In Table 1, TCDMA, TCDDA, and TCDAA represent compounds below, CP oligomers represent cyclopentadiene oligomers, and Hydroformylated CP oligomers represent hydroformylated cyclopentadiene oligomers.

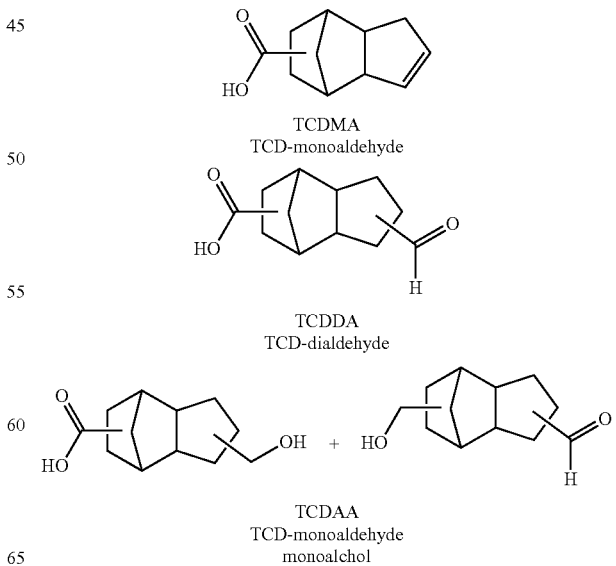

TCDMA
TCD-monoaldehyde

TCDDA
TCD-dialdehyde

TCDAA
TCD-monoaldehyde monoalchol

The experimental results showed that the desired TCDDA may be obtained with a high yield of 85% or more in Examples 1 to 15 in which the hydroformylation was performed stage by stage as in the present invention.

Further, components of the reaction mixture at each stage were analyzed by GC analysis. As a result, in the primary hydroformylation step performed by adding the DCPD solution dropwise at the relatively low temperature, TCDMA and TCDDA were produced at a ratio of about 1:1, and in the secondary hydroformylation step performed at the higher temperature, hydroformylation of TCDMA further occurred, and all TCDMA was converted to TCDDA, and thus TCDDA was prepared with high purity and high yield. As such, when the preparation method of the present invention is performed, the amounts of by-products such as TCDAA, CP oligomers, and hydroformylated CP oligomers were remarkably reduced.

In contrast, the large amounts of by-products such as CP oligomer, etc. were produced in Comparative Examples 1 and 2 in which the hydroformylation was not performed stage by stage, and thus the yield of TCDDA was low and purity thereof was also low. Further, the conversion rate to TCDDA was relatively excellent but the considerably large amounts of impurities such as TCDAA and CP oligomers were produced in Comparative Example 3 in which the DCPD solution was not added dropwise but added at once to the catalyst composition while performing the hydroformylation stage by stage.

The invention claimed is:

1. A method of preparing 3(4),8(9)-bisformyltricyclo [$5.2.1.0^{2,6}$]decane, the method comprising the steps of:
performing a primary hydroformylation reaction while adding dicyclopentadiene dropwise to a reactor having a first temperature and a first pressure in the presence of a catalyst composition including a rhodium-containing catalyst compound and an organophosphorus compound; and
performing a secondary hydroformylation reaction under a second temperature and a second pressure by increasing at least one of the pressure and the temperature of the reactor, after completing the primary hydroformylation reaction
wherein the primary and secondary hydroformylation reactions are performed under a mixed gas atmosphere of hydrogen and carbon monoxide,
wherein the dropwise addition of dicyclopentadiene is performed such that the number of moles of dicyclopentadiene introduced per minute with respect to 1 mmol of the rhodium atom in the catalyst composition is 10 mmol to 10000 mmol, and
wherein the rhodium-containing catalyst compound is used in an amount of 1 ppm to 50 ppm in terms of rhodium, based on the total weight of the dicyclopentadiene.

2. The method of preparing 3(4),8(9)-bisformyltricyclo [$5.2.1.0^{2,6}$]decane of claim 1, wherein the second temperature is 15° C. higher than the first temperature.

3. The method of preparing 3(4),8(9)-bisformyltricyclo [$5.2.1.0^{2,6}$]decane of claim 1, wherein the second pressure is 10 bar higher than the first pressure.

4. The method of preparing 3(4),8(9)-bisformyltricyclo [$5.2.1.0^{2,6}$]decane of claim 1, wherein the first temperature is 50° C. to 90° C.

5. The method of preparing 3(4),8(9)-bisformyltricyclo [$5.2.1.0^{2,6}$]decane of claim 1, wherein the first pressure is 20 bar to 130 bar.

6. The method of preparing 3(4),8(9)-bisformyltricyclo [$5.2.1.0^{2,6}$]decane of claim 1, wherein the second temperature is 80° C. to 180° C.

7. The method of preparing 3(4),8(9)-bisformyltricyclo [$5.2.1.0^{2,6}$]decane of claim 1, wherein the second pressure is 30 bar to 250 bar.

8. The method of preparing 3(4),8(9)-bisformyltricyclo [$5.2.1.0^{2,6}$]decane of claim 1, wherein the rhodium-containing catalyst compound and the organophosphorus compound are included at a molar ratio of 1:2 to 1:500, in terms of rhodium and phosphorus atoms.

9. The method of preparing 3(4),8(9)-bisformyltricyclo [$5.2.1.0^{2,6}$]decane of claim 1, wherein the rhodium-containing catalyst compound is one or more selected from the group consisting of $Rh(acac)(CO)_2$, $Rh_2O_3$, $Rh_4(CO)_{12}$, $Rh_6(CO)_{16}$, $Rh(NO_3)_3$, $Rh(CO_2(C1\sim C8))$, Rh/Al, and Rh/C.

10. The method of preparing 3(4),8(9)-bisformyltricyclo [$5.2.1.0^{2,6}$]decane of claim 1, wherein the organophosphorus compound is one or more selected from the group consisting of triphenylphosphite, tris(2-t-butylphenyl)phosphite, tris(3-methyl-6-t-butylphenyl)phosphite, tris(3-methoxy-6-t-butylphenyl)phosphite, tris(2,4-di-t-butylphenyl)phosphite, and di(2-t-butylphenyl)phosphite.

11. The method of preparing 3(4),8(9)-bisformyltricyclo [$5.2.1.0^{2,6}$]decane of claim 1, wherein a concentration of the catalyst composition is 0.01 mM to 5.0 mM in terms of the rhodium atoms.

* * * * *